(12) United States Patent
Wilson et al.

(10) Patent No.: US 8,383,697 B2
(45) Date of Patent: Feb. 26, 2013

(54) SYSTEMS FOR SELF-HEALING COMPOSITE MATERIALS

(75) Inventors: Gerald O. Wilson, Champaign, IL (US);
Mary M. Caruso, Urbana, IL (US);
Benjamin J. Blaiszik, Urbana, IL (US);
James W. Henderson, Winnetka, IL (US); Christopher Britt, St. Louis, MO (US); Jeffrey S. Moore, Savoy, IL (US);
Scott R. White, Champaign, IL (US);
Nancy R. Sottos, Champaign, IL (US)

(73) Assignee: Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 12/769,904

(22) Filed: Apr. 29, 2010

(65) Prior Publication Data
US 2010/0331445 A1 Dec. 30, 2010

Related U.S. Application Data

(60) Provisional application No. 61/174,214, filed on Apr. 30, 2009.

(51) Int. Cl.
*A61K 6/00* (2006.01)
*C09K 3/00* (2006.01)
(52) U.S. Cl. ............... 523/120; 106/35; 523/116
(58) Field of Classification Search .......... 523/120, 523/116; 106/35
See application file for complete search history.

(56) References Cited

U.S. PATENT DOCUMENTS

| | | | | | |
|---|---|---|---|---|---|
| 3,855,040 | A | * | 12/1974 | Malofsky | 156/310 |
| 4,417,028 | A | * | 11/1983 | Azevedo | 525/285 |
| 5,397,812 | A | * | 3/1995 | Usami et al. | 522/13 |
| 5,635,546 | A | * | 6/1997 | Rich et al. | 523/176 |
| 6,518,330 | B2 | * | 2/2003 | White et al. | 523/200 |
| 6,858,659 | B2 | | 2/2005 | White et al. | |
| 7,566,747 | B2 | * | 7/2009 | Moore et al. | 523/205 |
| 7,569,625 | B2 | * | 8/2009 | Keller et al. | 523/211 |
| 7,612,152 | B2 | * | 11/2009 | Braun et al. | 525/476 |
| 7,723,405 | B2 | | 5/2010 | Braun et al. | |
| 2005/0148739 | A1 | * | 7/2005 | Hara et al. | 525/452 |
| 2006/0111469 | A1 | | 5/2006 | White et al. | |
| 2006/0252852 | A1 | * | 11/2006 | Braun et al. | 523/200 |
| 2007/0004817 | A1 | * | 1/2007 | Hara et al. | 522/90 |
| 2008/0299391 | A1 | | 12/2008 | White et al. | |
| 2008/0300340 | A1 | * | 12/2008 | Gross et al. | 523/120 |
| 2008/0305343 | A1 | | 12/2008 | Toohey et al. | |
| 2009/0181254 | A1 | | 7/2009 | White et al. | |
| 2009/0191402 | A1 | | 7/2009 | Beiermann et al. | |
| 2010/0075134 | A1 | | 3/2010 | Blaiszik et al. | |
| 2010/0206088 | A1 | | 8/2010 | Potisek et al. | |
| 2011/0039980 | A1 | | 2/2011 | Caruso et al. | |

FOREIGN PATENT DOCUMENTS

WO  WO 2008147366 A1 * 12/2008

OTHER PUBLICATIONS

Wilson, G.O., Chapter 6 of Ph.D. Thesis, 2007, Publisher: University of Illinois at Urbana—Champaign.*

(Continued)

*Primary Examiner* — James J Seidleck
*Assistant Examiner* — Peter A Salamon
(74) *Attorney, Agent, or Firm* — Blanchard & Associates

(57) ABSTRACT

A composite material precursor composition includes a matrix precursor, a first plurality of capsules including a liquid polymerizer, an activator, and an accelerant. The liquid polymerizer polymerizes when in contact with the activator, and the accelerant is an accelerant for the polymerization of the liquid polymerizer. The composite material precursor may be used to form a composite material that includes a solid polymer matrix, the first plurality of capsules in the solid polymer matrix, the activator in the solid polymer matrix, and the accelerant in the solid polymer matrix.

20 Claims, 8 Drawing Sheets

OTHER PUBLICATIONS

Vazquez, et al., "Application of tertiary amines with reduced toxicity to the curing process of acrylic bone cements", "Journal of Biomedical Materials Research", 1997, pp. 129-136, vol. 34.

Wilson, G.O., "Chapter 6 of Ph.D. Thesis", 2007, Publisher: University of Illinois at Urbana—Champaign.

* cited by examiner

SYSTEMS FOR SELF-HEALING COMPOSITE MATERIALS

REFERENCE TO RELATED APPLICATIONS

This application claims the benefit of U.S. Provisional Application No. 61/174,214 entitled "Functionalized Particles For Self-Healing Composite Materials" filed Apr. 30, 2009, which is incorporated by reference in its entirety.

FEDERALLY SPONSORED RESEARCH OR DEVELOPMENT

This invention was made with government support under contract number(s) FA9550-06-1-0553 and FA9550-05-1-0346 awarded by the Air Force Office of Scientific Research MURI, and under contract number(s) DMI 0328162 awarded by the National Science Foundation. The government has certain rights in the invention.

BACKGROUND

Cracks that form within materials can be difficult to detect and almost impossible to repair. A successful method of autonomically repairing cracks that has the potential for significantly increasing the longevity of materials has been described, for example, in U.S. Pat. No. 6,518,330. This self-healing system includes a material containing, for example, solid particles of Grubbs catalyst and capsules containing liquid dicyclopentadiene (DCPD) embedded in an epoxy matrix. When a crack propagates through the material, it ruptures the microcapsules and releases DCPD into the crack plane. The DCPD then contacts the Grubbs catalyst, undergoes Ring Opening Metathesis Polymerization (ROMP), and cures to provide structural continuity where the crack had been.

Materials used in medical implants could benefit from having autonomic self-healing properties. Failure of these materials can be harmful or even fatal to the patient, and may require surgical intervention to repair the damage or to replace the material. In one example, fatigue and/or failure of bone cements used in artificial hip or knee implants can result in the formation of debris particles. These particles can contribute to aseptic loosening, in which inflammation of the natural tissue leads to bone destruction and loosening of the prosthesis. In 2004, revision surgeries performed in the U.S. to repair or replace hip or knee implants cost over $3 billion in hospitalization fees.

Bone cement based on poly(methyl methacrylate) (PMMA) has emerged as one of the premier synthetic biomaterials in contemporary orthopedics, and is used for anchoring prostheses to the contiguous bone in cemented arthroplasties. The bone cement formulation typically includes a liquid component and a solid component. The liquid component includes methyl methacrylate (MMA) monomer, and typically includes a tertiary aromatic amine accelerant such as dimethylamino-p-toluidine (DMPT) or dimethylaniline (DMA). The solid component includes a polymerization initiator such as benzoyl peroxide (BPO), a combination of PMMA and poly(styrene-co-methyl methacrylate) beads, and a radiopacifier such as barium sulfate. The liquid and solid components are mixed together just before use to form a grouting material that quickly sets due to polymerization of the MMA monomer.

Bone cement has a number of disadvantages. Toxicity of some of the reactants can lead to chemical necrosis. The high exotherm of the polymerization of MMA to PMMA can lead to thermal necrosis. Weak link zones can be formed, particularly at the bone-cement interface and at the cement-prosthesis interface. These disadvantages can contribute to aseptic loosening and/or other complications during and/or after surgery, and often lead to revision surgery.

Attempts at developing a self-healing bone cement have included using a polyester matrix material; a monomer mixture containing 35 weight percent (wt %) styrene, 35 wt % divinyl benzene and polystyrene (35 wt %); an accelerant containing cobalt (II) naphthenate and DMA; and methyl ethyl ketone peroxide (MEKP) as an initiator for the polymerization of the monomer mixture (Hegeman, A. J. *Self Repairing Polymers: Repair Mechanisms and Micromechanical Modeling*; Master of Science thesis; University of Illinois at Urbana-Champaign: Urbana, Ill., 1997). These attempts have met with mixed success, and likely have suffered from an insufficient amount of initiator in the crack plane of the damaged bone cement.

It is desirable to provide a self-healing bone cement material. It is also desirable to provide a self-healing material in which the healing is more rapid and/or robust than in conventional self-healing materials.

SUMMARY

In one aspect, the invention provides a composite material precursor composition that includes a matrix precursor, a first plurality of capsules including a liquid polymerizer, an activator, and an accelerant. The liquid polymerizer polymerizes when in contact with the activator, and the accelerant is an accelerant for the polymerization of the liquid polymerizer.

In another aspect, the invention provides a composite material that includes a solid polymer matrix, a first plurality of capsules in the solid polymer matrix, an activator in the solid polymer matrix, and an accelerant in the solid polymer matrix. The first plurality of capsules includes a liquid polymerizer, and the liquid polymerizer polymerizes when in contact with the activator. The accelerant is an accelerant for the polymerization of the liquid polymerizer.

In another aspect, the invention provides a composite material that includes a solid polymer matrix, a first plurality of capsules in the solid polymer matrix, an activator in the solid polymer matrix, and a plurality of functionalized particles in the solid polymer matrix. The first plurality of capsules includes a liquid polymerizer, and the liquid polymerizer polymerizes when in contact with the activator. The functionalized particles include particles having a surface, and a functional group immobilized on the surface of the particles. The functional group includes an accelerant for the polymerization of the polymerizer.

In another aspect, the invention provides a method of making a composite material that includes combining ingredients including a matrix precursor, a first plurality of capsules including a liquid polymerizer, an activator and an accelerant; and solidifying the matrix precursor to form a solid polymer matrix. The liquid polymerizer polymerizes when in contact with the activator, and the accelerant is an accelerant for the polymerization of the liquid polymerizer.

To provide a clear and more consistent understanding of the specification and claims of this application, the following definitions are provided.

The term "polymer" means a substance containing more than 100 repeat units. The term "polymer" includes soluble and/or fusible molecules having long chains of repeat units, and also includes insoluble and infusible networks. The term "prepolymer" means a substance containing less than 100 repeat units and that can undergo further reaction to form a polymer.

The term "matrix" means a continuous phase in a material.

The term "capsule" means a hollow, closed object having an aspect ratio of 1:1 to 1:10, and that may contain a solid, liquid, gas, or combinations thereof. The aspect ratio of an object is the ratio of the shortest axis to the longest axis, where these axes need not be perpendicular. A capsule may have any shape that falls within this aspect ratio, such as a sphere, a toroid, or an irregular ameboid shape. The surface of a capsule may have any texture, for example rough or smooth.

The term "on", in the context of a particle and a functional group, means supported by. A functional group that is on a particle may be separated from the particle by one or more other substances, such as an adhesion promoter or another functional group. The functional group may or may not be above the particle during the formation or use of the functionalized particle.

The term "healing agent" means a substance that can contribute to the restoration of structural integrity to an area of a material that has been subjected to damage. Examples of healing agents include polymerizers, activators for polymerizers, accelerants, solvents, and mixtures of these.

The term "polymerizer" means a composition that will form a polymer when it comes into contact with a corresponding activator for the polymerizer. Examples of polymerizers include monomers of polymers, such as styrene, ethylene, acrylates, methacrylates and dicyclopentadiene (DCPD); one or more monomers of a multi-monomer polymer system, such as diols, diamines and epoxides; prepolymers such as partially polymerized monomers still capable of further polymerization; and functionalized polymers capable of forming larger polymers or networks.

The term "activator" means anything that, when contacted or mixed with a polymerizer, will form a polymer. Examples of activators include catalysts and initiators. A corresponding activator for a polymerizer is an activator that, when contacted or mixed with that specific polymerizer, will form a polymer.

The term "catalyst" means a compound or moiety that will cause a polymerizable composition to polymerize, and that is not always consumed each time it causes polymerization. This is in contrast to initiators, which are always consumed at the time they cause polymerization. Examples of catalysts include ring opening metathesis polymerization (ROMP) catalysts such as Grubbs catalyst. Examples of catalysts also include silanol condensation catalysts such as titanates and dialkyltincarboxylates. A corresponding catalyst for a polymerizer is a catalyst that, when contacted or mixed with that specific polymerizer, will form a polymer.

The term "initiator" means a compound or moiety that will cause a polymerizable composition to polymerize and, in contrast to a catalyst, is always consumed at the time it causes polymerization. Examples of initiators include peroxides, which can form a radical to cause polymerization of an unsaturated monomer; a monomer of a multi-monomer polymer system, such as a diol, a diamine, and an epoxide; and amines, which can form a polymer with an epoxide. A corresponding initiator for a polymerizer is an initiator that, when contacted or mixed with that specific polymerizer, will form a polymer.

The term "accelerant" means a substance that increases the rate of a polymerization reaction without being consumed.

The term "solvent", in the context of a healing agent, means a liquid that can dissolve another substance, and that is not a polymerizer.

The term "encapsulant" means a material that will dissolve or swell in a polymerizer and, when combined with an activator, will protect the activator from reaction with materials used to form a solid polymer matrix. A corresponding encapsulant for a solid polymer matrix and for a polymerizer will protect an activator from reaction with materials used to form that specific solid polymer matrix and will dissolve or swell in that specific polymerizer.

The term "matrix precursor" means a composition that will form a polymer matrix when it is solidified. A matrix precursor may include a monomer and/or prepolymer that can polymerize to form a solid polymer matrix. A matrix precursor may include a polymer that is dissolved or dispersed in a solvent, and that can form a solid polymer matrix when the solvent is removed. A matrix precursor may include a polymer at a temperature above its melt temperature, and that can form a solid polymer matrix when cooled to a temperature below its melt temperature.

BRIEF DESCRIPTION OF THE DRAWINGS

The invention can be better understood with reference to the following drawings and description. The components in the figures are not necessarily to scale and are not intended to accurately represent molecules or their interactions, emphasis instead being placed upon illustrating the principles of the invention.

DETAILED DESCRIPTION

In accordance with the present invention a composite material precursor composition includes a matrix precursor, a first plurality of capsules including a liquid polymerizer, an activator, and an accelerant. The liquid polymerizer polymerizes when in contact with the activator, and the accelerant is an accelerant for the polymerization of the liquid polymerizer. The composite material precursor may be used to form a composite material that includes a solid polymer matrix, the first plurality of capsules in the solid polymer matrix, the activator in the solid polymer matrix, and the accelerant in the solid polymer matrix.

In one example, a composite material includes a solid polymer matrix, a first plurality of capsules in the solid polymer matrix, an activator in the solid polymer matrix, and a plurality of functionalized particles in the solid polymer matrix. The first plurality of capsules includes a liquid polymerizer, which polymerizes when in contact with the activator. The functionalized particles include a particle having a surface, and a functional group immobilized on the surface of the particle. The functional group is an accelerant for the polymerization of the polymerizer.

Figure 1:
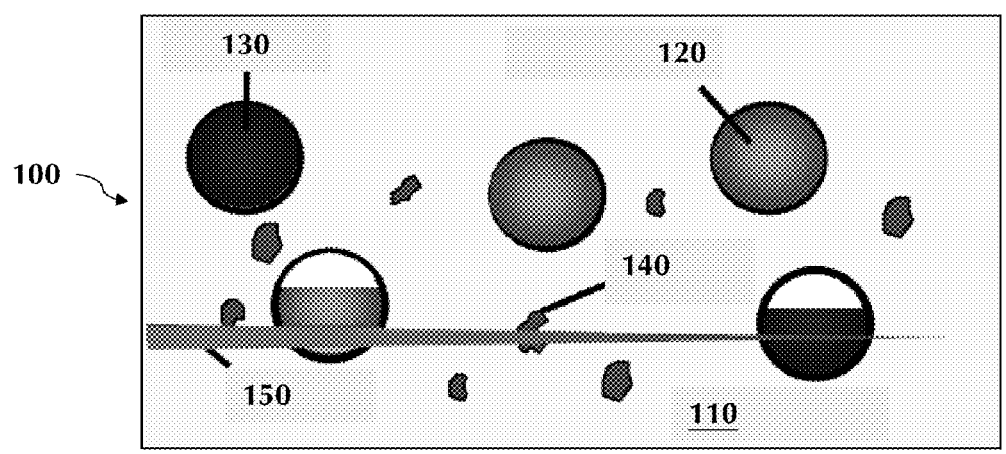
FIG. 1 depicts a schematic representation of a composite material including capsules containing a liquid polymerizer, an activator, and functionalized particles.

FIG. 1 is a schematic representation of a composite material 100 that includes a solid polymer matrix 110, a first plurality of capsules 120 in the solid polymer matrix, an activator in the solid polymer matrix, and a plurality of functionalized particles 140 in the solid polymer matrix. The first plurality of capsules 120 includes a liquid polymerizer, which polymerizes when in contact with the activator. The activator may be present in optional activator particles 130.

The solid polymer matrix 110 may include a polyamide such as nylon; a polyester such as poly(ethylene terephthalate) and polycaprolactone; a polycarbonate; a polyether; an epoxy polymer; an epoxy vinyl ester polymer; a polyimide such as polypyromellitimide (for example KAPTAN); a phenol-formaldehyde polymer such as BAKELITE; an amine-formaldehyde polymer such as a melamine polymer; a polysulfone; a poly(acrylonitrile-butadiene-styrene) (ABS); a polyurethane; a polyolefin such as polyethylene, polystyrene, polyacrylonitrile, a polyvinyl, polyvinyl chloride and poly(DCPD); a polyacrylate such as poly(ethyl acrylate); a poly(alkylacrylate) such as poly(methyl methacrylate); a polysilane such as poly(carborane-silane); and a polyphosphazene. The solid polymer matrix 110 may include an elastomer, such as an elastomeric polymer, an elastomeric copolymer, an elastomeric block copolymer, and an elastomeric polymer blend. Self-healing materials that include an elastomer as the solid polymer matrix are disclosed, for example, in U.S. Pat. No. 7,569,625. The solid polymer matrix 110 may include a mixture of these polymers, including copolymers that include repeating units of two or more of these polymers, and/or including blends of two or more of these polymers.

Preferably the solid polymer matrix includes a polymer containing acrylate and/or alkyl acrylate monomer units. More preferably the solid polymer matrix includes a polymer containing methacrylate units, and more preferably containing methyl methacrylate units. In one example, the solid polymer matrix is poly(methyl methacrylate) PMMA.

The solid polymer matrix 110 may include other ingredients in addition to the polymeric material. For example, the matrix may contain one or more stabilizers, antioxidants, flame retardants, plasticizers, colorants and dyes, fragrances, or adhesion promoters. An adhesion promoter is a substance that increases the adhesion between two substances, such as the adhesion between two polymers. One type of adhesion promoter that may be present includes substances that promote adhesion between the solid polymer matrix 110 and the capsules 120, and/or between the solid polymer matrix 110 and the optional activator particles 130. The adhesion between the matrix and the capsules may influence whether the capsules will rupture or debond when a crack is formed in the composite. To promote one or both of these forms of adhesion, various silane coupling agents may be used. Another type of adhesion promoter that may be present includes substances that promote adhesion between the solid polymer matrix 110 and the polymer formed from the polymerizer. The adhesion between the matrix and this polymer may influence whether the composite can be healed once damage has occurred. To promote the adhesion between the solid polymer matrix and the polymer formed from the healing agent, various unsaturated silane coupling agents may be used.

The first plurality of capsules 120 isolates the liquid polymerizer in the capsules until the composite is subjected to damage that forms a crack in the composite. Once the damage occurs, the capsules in contact with the damaged area can rupture, releasing the liquid polymerizer into the crack plane.

The capsules 120 have an aspect ratio of from 1:1 to 1:10, preferably from 1:1 to 1:5, more preferably from 1:1 to 1:3, more preferably from 1:1 to 1:2, and more preferably from 1:1 to 1:1.5. In one example, the capsules may have an average diameter of from 10 nanometers (nm) to 1 millimeter (mm), more preferably from 30 to 500 micrometers, and more preferably from 50 to 300 micrometers. In another example, the capsules may have an average diameter less than 10 micrometers. Capsules having an average outer diameter less than 10 micrometers, and methods for making these capsules, are disclosed, for example, in U.S. Patent Application Publication 2008/0299391 with inventors White et al., published Dec. 4, 2008.

The capsules 120 are hollow, having a capsule wall enclosing an interior volume containing a liquid. The thickness of the capsule wall may be, for example, from 30 nm to 10 micrometers. For capsules having an average diameter less than 10 micrometers, the thickness of the capsule wall may be from 30 nm to 150 nm, or from 50 nm to 90 nm. The selection of capsule wall thickness may depend on a variety of parameters, such as the nature of the solid polymer matrix, and the conditions for making and using the composite. For example, a capsule wall that is too thick may not rupture when the interface with which it is in contact is damaged, while a capsules wall that is too thin may break during processing.

Hollow capsules may be made by a variety of techniques, and from a variety of materials. Examples of materials from which the capsules may be made, and the techniques for making them include: polyurethane, formed by the reaction of isocyanates with a diol; urea-formaldehyde (UF), formed by in situ polymerization; gelatin, formed by complex coacervation; polyurea, formed by the reaction of isocyanates with a diamine or a triamine, depending on the degree of crosslinking and brittleness desired; polystyrene or polydivinylbenzene formed by addition polymerization; and polyamide, formed by the use of a suitable acid chloride and a water soluble triamine. For capsules having an average diameter less than 10 micrometers, the capsule formation may include forming a microemulsion containing the capsule starting materials, and forming microcapsules from this microemulsion.

The liquid polymerizer of the first plurality of capsules 120 may include, for example, a monomer, a prepolymer, or a functionalized polymer having two or more reactive groups. Examples of polymerizers include alkene-functionalized monomers, prepolymers or polymers, which may form a polymer when contacted with other alkene groups. Examples of alkene-functionalized polymerizers include monomers such as acrylates; alkylacrylates including methacrylates and ethacrylates; olefins including styrenes, isoprene and butadiene; and cyclic olefins including dicyclopentadiene (DCPD), norbornene and cyclooctadiene. Examples of alkene-functionalized polymerizers also include diallyl phthalate (DAP), diallyl isophthalate (DAIP), triallyl isocyanurate, hexanediol diacrylate (HDDA), trimethylol propanetriacrylate (TMPTA), and epoxy vinyl ester prepolymers and polymers.

Preferably the liquid polymerizer includes acrylate and/or alkylacrylate monomers. Acrylate and/or alkylacrylate monomers typically have good reactivity in free radical polymerization. The resulting polymers can have desirable mechanical properties and have been used in a variety of biomedical applications. Examples of monomers include methyl methacrylate (MMA; structure I), butyl methacrylate (BMA; structure II), 2,2-bis[4(2-hydroxy-3-methacryloxypropoxy)phenol]propane (Bis-GMA; structure III), trimethylolpropane trimethacrylate (TMPTMA; structure IV), and ethylene glycol dimethacrylate (EGDMA; structure V):

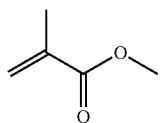

(I)

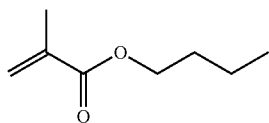

(II)

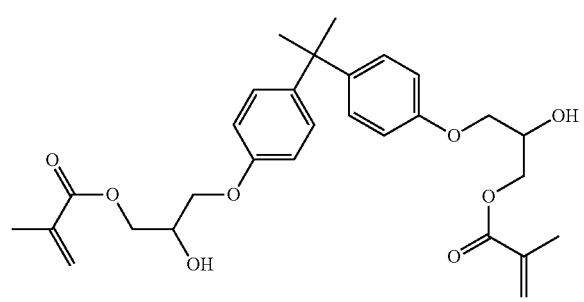

(III)

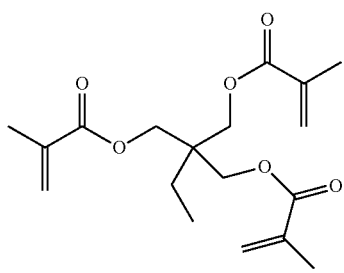

(IV)

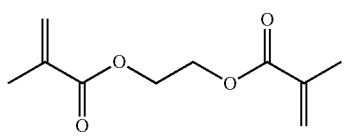

(V)

These monomers may be present alone or in combination with each other and/or with another alkene functional polymerizer. One example of another alkene functional polymerizer is styrene (structure VI):

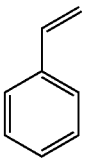

(VI)

A combination of monofunctional monomers, such as MMA, BMA and styrene, and multifunctional monomers, such as Bis-GMA, TMPTMA and EGDMA, is expected to be particularly useful in minimizing volume shrinkage of the liquid polymerizer and in improving polymerizer reactivity. Preferably the polymer resulting from the polymerization of the polymerizer has good strength.

The first plurality of capsules 120 may further include a solvent. Examples of capsules that include a polymerizer and a solvent are disclosed, for example, in copending U.S. patent application Ser. No. 12/739,537, with inventors Caruso et al., filed Apr. 23, 2010. The capsules may include an aprotic solvent, a protic solvent, or a mixture of these. Examples of aprotic solvents include hydrocarbons, such as cyclohexane; aromatic hydrocarbons, such as toluene and xylenes; halogenated hydrocarbons, such as dichloromethane; halogenated aromatic hydrocarbons, such as chlorobenzene and dichlorobenzene; substituted aromatic solvents, such as nitrobenzene; ethers, such as tetrahydrofuran (THF) and dioxane; ketones, such as acetone and methyl ethyl ketone; esters, such as ethyl acetate, hexyl acetate, ethyl phenylacetate (EPA) and phenylacetate (PA); tertiary amides, such as dimethyl acetamide (DMA), dimethyl formamide (DMF) and N-methylpyrrolidine (NMP); nitriles, such as acetonitrile; and sulfoxides, such as dimethyl sulfoxide (DMSO). Examples of protic solvents include water; alcohols, such as ethanol, isopropanol, butanol, cyclohexanol, and glycols; and primary and secondary amides, such as acetamide and formamide.

The capsules 120 may include other ingredients in addition to the liquid polymerizer and the optional solvent. For example, the capsules may contain one or more solvents, stabilizers, antioxidants, flame retardants, plasticizers, colorants and dyes, fragrances, or adhesion promoters.

The activator may be a general activator for polymerization, or a corresponding activator for a specific polymerizer present in the composite material. Preferably the activator is a corresponding activator for the liquid polymerizer present in the first plurality of capsules 120. The activator may be a catalyst or an initiator.

The activator may be a two-part activator, in which two distinct substances must be present in combination for the activator to function. In one example of a two-part activator system, a corresponding polymerizer may contain alkene-functional polymerizers. In this example, atom transfer radical polymerization (ATRP) may be used, with one of the activator components being present with the liquid healing agent, and the other activator component acting as the initiator. One component can be an organohalide such as 1-chloro-1-phenylethane, and the other component can be a copper(I) source such as copper(I) bipyridyl complex. In another exemplary system, one activator component could be a peroxide such as benzoyl peroxide, and the other activator component could be a nitroxo precursor such as 2,2,6,6-tetramethylpiperidinyl-1-oxy. These systems are described in Stevens et al., *Polymer Chemistry: An Introduction*, 3rd Edition; Oxford University Press, New York, (1999), pp. 184-186.

Preferably the activator is a free radical polymerization initiator. More preferably the activator is a free radical polymerization initiator that has low toxicity, high thermal stability and high reactivity. Examples of activators for free radical polymerization of the monomers shown above as structures I through VI include peroxide initiators. Examples of peroxide initiators include benzoyl peroxide (BPO; structure VII), lauroyl peroxide (LPO; structure VIII), methyl ethyl ketone peroxide (MEKP; structure IX), tert-butyl peroxide (TBP; structure X), tert-butyl peroxybenzoate (TBPB; structure XI):

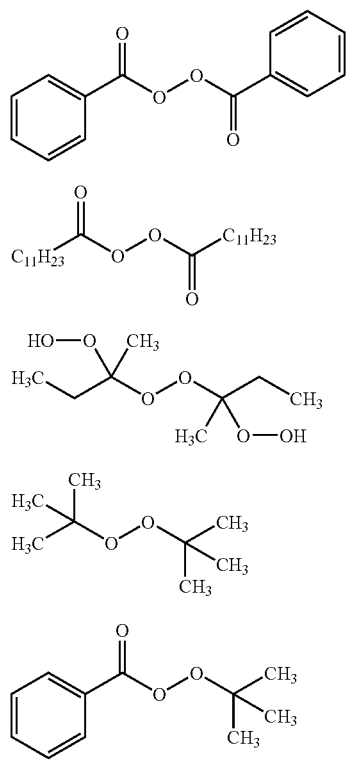

Table 1 below lists the toxicity, water solubility (Hatakeyama, T.; Quinn, F. *Applications of Thermal Analysis; Thermal Analysis: Fundamentals and Applications to Polymer Science;* 2$^{nd}$ ed.; Wiley and Sons: Chichester, England, 1994) and indicators of thermal stability for the initiators having structures VII to XI.

The LD50 value is the dosage of a substance required to kill half of a sample of test subjects. The LD50 values for sodium cyanide (6.4 mg/kg) and ethanol (7060 mg/kg) were selected as benchmark limits for toxicity, with sodium cyanide serving as the reference value for an acutely toxic compound, and ethanol serving as the point of comparison for a mildly toxic substance (Fisher Scientific, MSDS).

The melting points and boiling points (if applicable) of each initiator and the temperature at which the half life of the initiator is 10 hours (10 h half life T) can indicate the thermal stabilities of these five initiators. This data can be used to assess the compatibility of these or other initiators with potential processing conditions including the conditions for microencapsulation, reaction exotherms due to curing of the bone cement, and higher ambient temperature in vivo. Melting and boiling points can be used to assess the phases in which the initiators exist at room temperature, and evaluate their suitability for the temperatures that accompany the encapsulation process or other processing conditions. Since the system is to function at ambient temperatures of 37-38° C. in vivo and even higher temperatures during the curing of bone cement, an evaluation of thermal stability at elevated temperature offers insight into the suitability of a polymerization initiator for such conditions.

The activator may be present in solid form, such as crystals of the activator. These activator particles preferably are microparticles having an average diameter of at most 500 micrometers. Specific examples of pure activators in solid form include solid particles of Grubbs catalyst.

The activator may be present in optional activator particles 130. The activator may be present in a mixture with other ingredients, such as one or more stabilizers, antioxidants, flame retardants, plasticizers, colorants and dyes, fragrances, or adhesion promoters. The optional particles may be present in the form of solid particles, or as a second plurality of capsules. Optional activator particles 130 may be helpful in protecting the activator from the conditions required to form the composite 100 and/or from the conditions in which the composite will be used. For a two-part activator, one part of the activator may be in the optional activator particles 130, and the other part of the activator may be in the solid polymer matrix or in the first plurality of capsules 120.

The optional activator particles 130 may include a mixture of an activator and an encapsulant. These activator particles may be made by a variety of techniques, and from a variety of materials. For example, small particles or a powder of the activator may be dispersed into a liquid containing the encapsulant, followed by solidification of the mixture of encapsulant and activator. These activator particles preferably are microparticles having an average diameter of at most 500 micrometers. The encapsulant preferably is soluble in, or swells in, the liquid healing agent, and is a solid at room temperature. The liquid healing agent may dissolve the

TABLE 1

Properties of free radical initiators

| Initiator | Rat Oral LD50 (mg/kg) | Water Solubility | Melting Point (° C.) | Boiling Point (° C.) | 10 h Half Life T (° C.) |
|---|---|---|---|---|---|
| VII | 7,710 | <0.1 g/100 mL at 26° C. | 105-106 | N/A | 70 |
| VIII | 10,000 | Insoluble | 53 | N/A | 65 |
| IX | 484 | 0.1-0.5 g/100 mL at 22° C. | 110 | N/A | Not Listed |
| X | 25,000 | <0.1 g/100 mL at 21° C. | −40 | 109-110 | 70 |
| XI | 4,160 | <0.1 g/100 mL at 20° C. | 8 | 113 | 103 |

The toxicities of these five initiators were compared via LD50 (Lethal Dose, 50%) values obtained from experiments performed in rats (University of Oxford, Physical and Theoretical Chemistry Laboratory, MSDS, accessed Online June 2007; Fisher Scientific, MSDS, accessed online June 2007).

encapsulant, releasing the activator and forming a polymer. The liquid healing agent may swell the encapsulant so that the particle can be penetrated by the liquid healing agent sufficiently to allow polymerization of a polymerizer of the liquid healing agent upon contact with the activator. Examples of particles that include an activator and an encapsulant are disclosed, for example, in U.S. Pat. No. 7,566,747.

The optional activator particles 130 may include capsules, and a liquid that includes the activator in the capsules. This second plurality of capsules may be as described above for the first plurality of capsules, and may include other ingredients in addition to the activator. For example, the second plurality of capsules may contain one or more stabilizers, antioxidants, flame retardants, plasticizers, colorants and dyes, fragrances, or adhesion promoters.

The functionalized particles 140 include particles having a surface, and a functional group immobilized on the surface of the particles. The particles may include an inorganic and/or an organic material. Examples of particulate materials include carbon black, ceramic particles, metal particles, and polymer particles. Preferably the particles include hydroxyapatite (HA). Hydroxyapatite (HA) has become widely used in orthopedic applications. Advantages of HA include its osteoconductivity and osteoinductivity, and its ability to improve the mechanical properties of PMMA-based bone cements without detrimental effects on stress distribution or flow of the cement.

The functional group immobilized on the surface of the particles is an accelerant for the polymerization of the polymerizer. An accelerant is a substance that increases the rate of a polymerization reaction without being consumed. Examples of accelerants for free radical polymerizations include N,N-dimethylaniline (DMA; structure XII), 4,N,N-timethylaniline (DMT; structure XIII), and 4,4'-methylene-bis(N,N-dimethyl)aniline (MBDMA; structure XIV), below. Derivatives of these or other accelerants may be immobilized on the surfaces of particles.

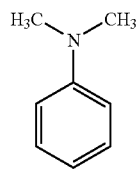

(XII)

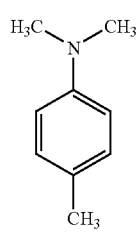

(XIII)

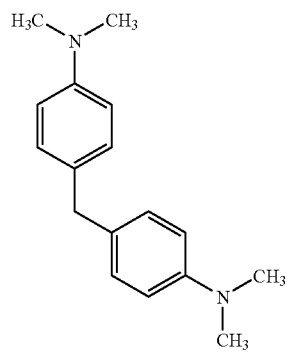

(XIV)

The functionalized particles 140 may be prepared by a variety of techniques. In one example, a monomer including an accelerant functional group is polymerized on the surface of a particle. In this example, the functionalized particle includes a polymer on its surface, where the polymer includes multiple accelerant functional groups. An example of a monomer including an accelerant functional group is dimethylaminobenzyl methacrylate. This method of forming functionalizing particles 140 is preferred, since it may be possible to provide a higher density of accelerant functional groups than is possible with the method described below. Since an immobilized accelerant may have lower mobility in a reaction than the corresponding non-immobilized accelerant, a higher density of the accelerant functional groups may help compensate for the lower mobility.

Figure 2:
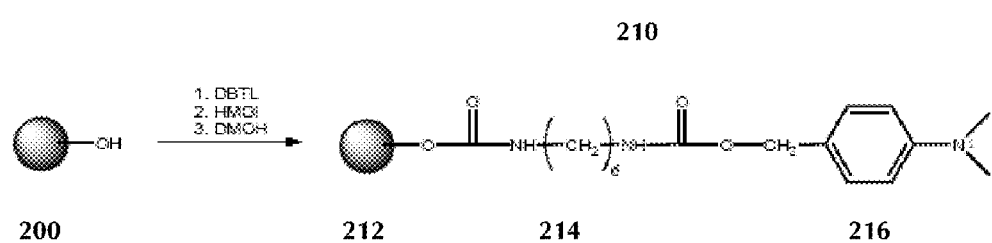
FIG. 2 depicts the formation of a functionalized particle.

In another example, a bifunctional group is used to link the particle and the accelerant functional group. In this example, a bifunctional linking group such as a diisocyante is bonded to the surface of a particle through reaction of one of the isocyanate groups with a functional group on the surface. The remaining isocyanate group is then reacted with a functional group of the derivative of the accelerant. FIG. 2 depicts the formation of a functionalized particle, in which a particle 200 having a hydroxyl group on the surface is reacted with reagents to form the functionalized particle 210 including a particle 212, a bifunctional linking group 214 and an accelerant functional group 216. The reagents in this example included hexamethylene diisocyanate (HMDI) as the precursor to the linking group 214, dibutyltin dilaurate (DBTL) to catalyze the reaction of the HMDI with the hydroxyl-functional HA 210, and dimethylaminobenzyl alcohol (DMOH). The DMOH reagent includes the N,N-dimethylaniline structure that is present in accelerants XII, XIII and XIV, and also includes a hydroxyl functional group for reaction with an isocyanate group of the immobilized HMDI derivative. Thus, the accelerant functional group 216 also includes the N,N-dimethylaniline structure that is present in accelerants XII, XIII and XIV.

Figure 3:
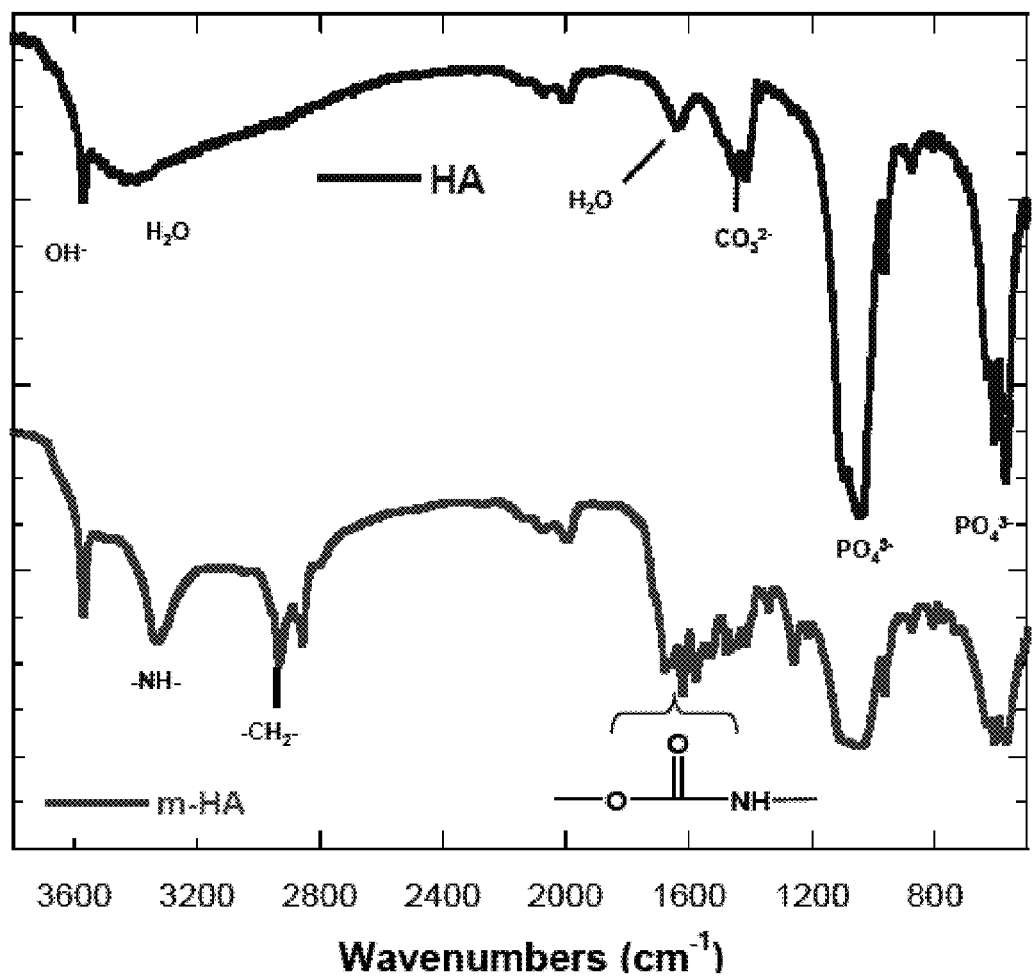
FIG. 3 depicts infrared spectra of hydroxyapatite (HA) and dimethylaminobenzyl alcohol-modified HA (m-HA).

FIG. 3 represents IR spectra of HA particles and of dimethylaminobenzyl alcohol-modified HA particles (m-HA). The spectrum of m-HA included peaks near 3328 cm$^{-1}$, 2850-2940 cm$^{-1}$ and 1570-1680 cm$^{-1}$ which were not present in the spectrum of HA. These peaks correspond to —NH—, —CH$_2$—, —CO—NH, and —C=O amide bands, respectively, indicating grafting of the DMOH to the surface of the HA.

Figure 4:
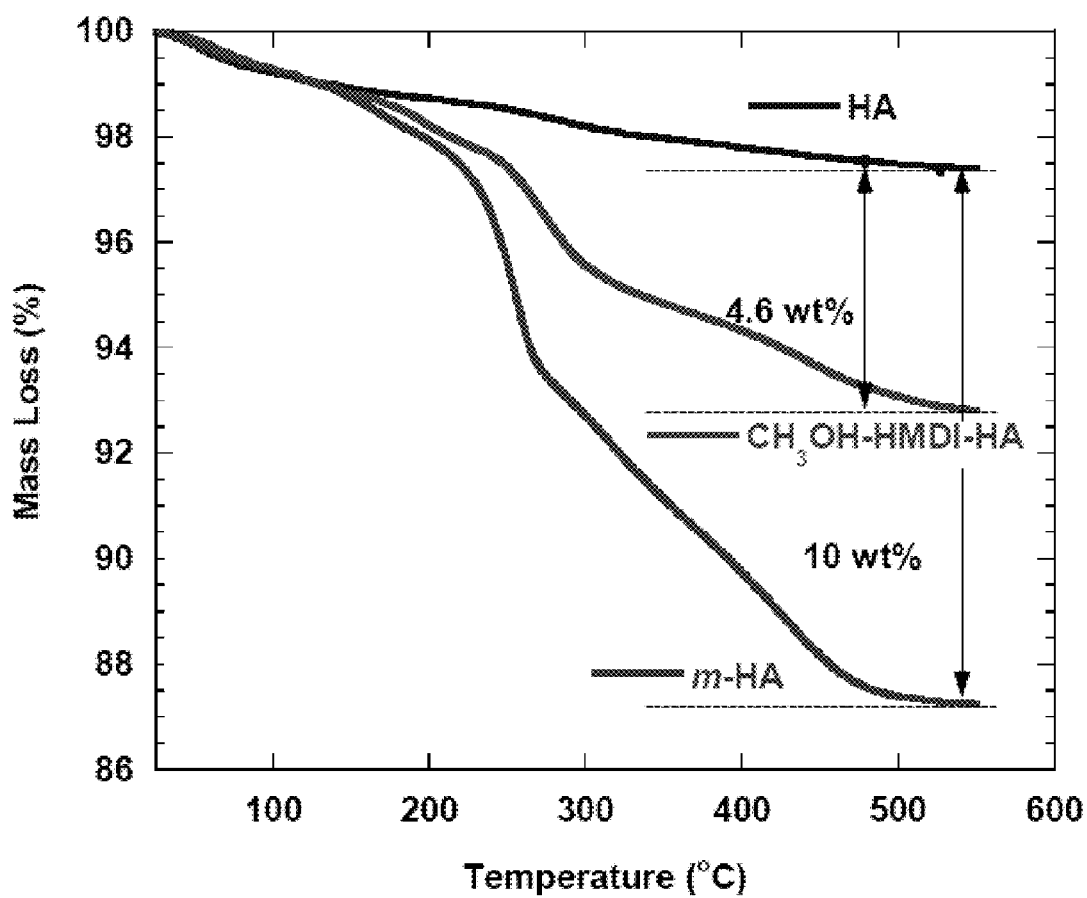
FIG. 4 depicts TGA data for HA, dimethylaminobenzyl alcohol-modified HA (m-HA), and HA functionalized by HMDI alone and quenched with methanol.

FIG. 4 represents graphs of weight loss as a function of temperature, as measured by thermogravimetric analysis (TGA), for particles of either HA, m-HA or HA modified with a methoxy group instead of a dimethylamino benzyoxy group. From this data, the grafting density of DMOH on m-HA was calculated as 0.31 grams per millimole (g/mmol).

Figure 5:
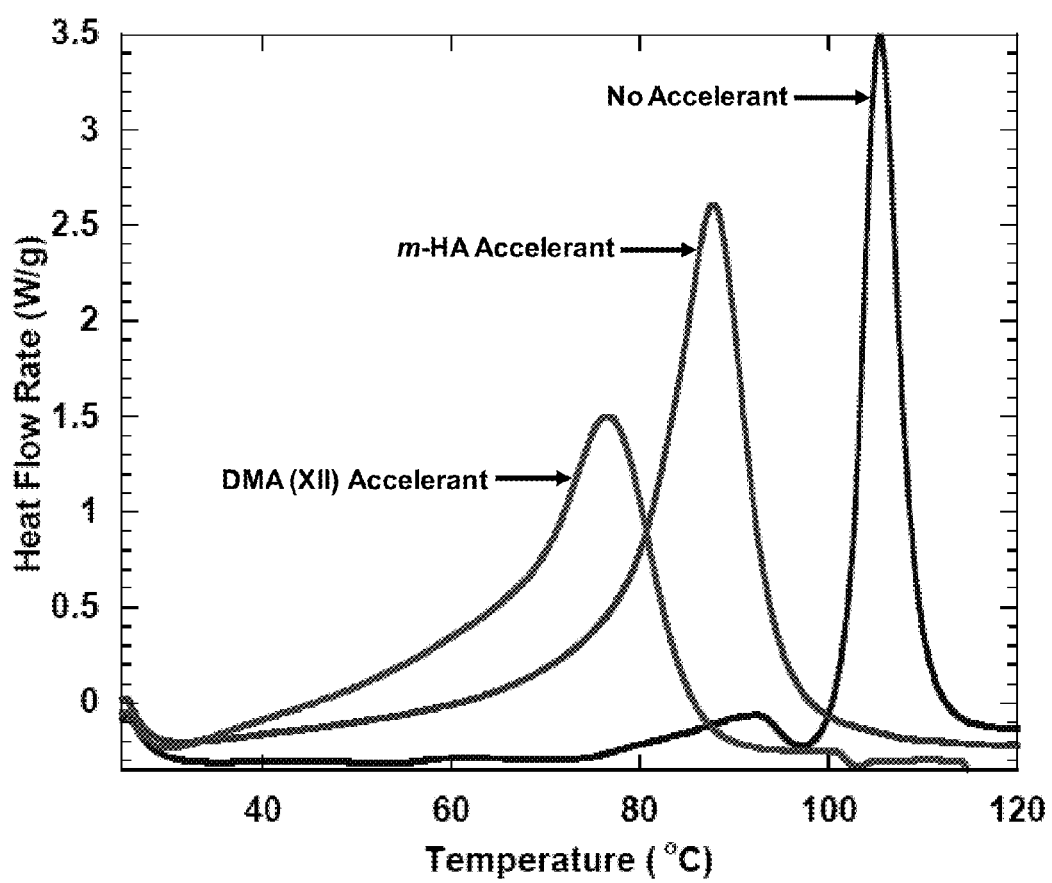
FIG. 5 depicts dynamic DSC data for the curing reactions of a bone cement mimic containing no accelerant, m-HA as an accelerant and dimethylaniline (DMA) as an accelerant.

FIG. 5 represents graphs of heat flow as a function of temperature, as measured by dynamic differential scanning calorimetry (DSC), for simulated bone cement reactions. For the graph labeled "No Accelerant", the reaction mixture included 54.1 wt % PMMA beads, 5.4 wt % initiator VII, 40.5 wt % HA and 2 mL MMA monomer. For the graph labeled "DMA (XII) Accelerant", the reaction mixture was identical to the first mixture, except that 0.02 mL of accelerant XII was added. For the graph labeled "m-HA Accelerant", the reaction mixture was identical to the first mixture, except that m-HA was used instead of HA. Based on an estimation of 6.1 wt % accelerant functional groups in every sample of m-HA, the number of moles of accelerant in the sample containing m-HA was calculated to be $3.06 \times 10^{-4}$ mol, while the number of moles of accelerant in the sample containing DMA accelerant was $1.58 \times 10^{-4}$ mol. Compared to the sample containing no accelerant, significant polymerization acceleration was observed for the sample containing m-HA.

The composite material such as 100 may be self-healing. When the composite 100 is subjected to a crack, the liquid polymerizer from the capsules 120 can flow into the crack, contacting the activator and accelerant and forming a polymer. The crack faces in the solid polymer matrix 110 are thus bonded to each other or to the polymer formed in the crack. It is desirable for the first plurality of capsules, the activator, and the functionalized particles 140 to be dispersed throughout the composite, so that a crack will intersect and break one or more capsules 120, releasing the liquid polymerizer, and so that the released liquid polymerizer can contact the activator and the accelerant functional group of the functionalized particle 140.

A method of making a composite material, such as composite material 100, includes combining ingredients including a matrix precursor, a first plurality of capsules, an activator and a plurality of functionalized particles. The method further includes solidifying the matrix precursor to form a solid polymer matrix. The first plurality of capsules includes a liquid polymerizer, and the activator is an activator for the polymerizer. The functionalized particles include a particle having a surface and a functional group immobilized on the surface. The functional group includes an accelerant for the polymerization of the polymerizer. The method may further include forming the functionalized particles. The matrix precursor may be any substance that can form a solid polymer matrix when solidified.

In one example, the matrix precursor includes a monomer and/or prepolymer that can polymerize to form a polymer. The capsules, activator and functionalized particles may be mixed with the monomer or prepolymer. The matrix precursor may then be solidified by polymerizing the monomer and/or prepolymer of the matrix precursor to form the solid polymer matrix.

In another example, the matrix precursor includes a polymer in a matrix solvent. The polymer may be dissolved or dispersed in the matrix solvent to form the matrix precursor, and the capsules, activator and functionalized particles then mixed into the matrix precursor. The matrix precursor may be solidified by removing at least a portion of the matrix solvent from the composition to form the solid polymer matrix.

In another example, the matrix precursor includes a polymer that is at a temperature above its melting temperature. The polymer may be melted to form the matrix precursor and then mixed with the capsules, activator and functionalized particles. The matrix precursor may be solidified by cooling the composition to a temperature below the melt temperature of the polymer to form the solid polymer matrix.

The following examples are provided to illustrate one or more preferred embodiments of the invention. Numerous variations can be made to the following examples that lie within the scope of the invention.

EXAMPLES

Materials

Non-sintered hydroxyapatite (HA; Merck: Whitehouse Station, N.J.) was dried at 120° C. for at least 24 h before use. Hexamethylene diisocyanate (HMDI; Sigma Aldrich: St. Louis, Mo.), dibutyltin dilaurate (DBTL, Sigma Aldrich), toluene diisocyanate (TDI; Sigma Aldrich), tert-butyl peroxide (TBP; initiator X; Sigma Aldrich), methyl ethyl ketone peroxide (MEKP; initiator IX; Sigma Aldrich), and tert-butyl peroxybenzoate (TBPB; initiator XI; Acros: Geel, Belgium), N,N-dimethylaniline (DMA; accelerant XII; Sigma Aldrich), 4,N,N-timethylaniline (DMT; accelerant XIII; Fluka), and 4,4'-methylene-bis(N,N-dimethyl)aniline (MBDMA; accelerant XIV; Acros), 2,2-bis[4(2-hydroxy-3-methacryloxypropoxy)phenol]propane (Bis-GMA; monomer III; Sigma Aldrich), trimethylolpropane trimethacrylate (TMPTMA; monomer IV; Sigma Aldrich) and ethylene glycol trimethacrylate (EGDMA; monomer V; Sigma Aldrich) were used as-received. Benzoyl peroxide (BPO; initiator VII; Sigma Aldrich) and lauroyl peroxide (LPO; initiator VIII; Sigma Aldrich) were ground into a fine powder before use. The resin Derakane® 510A-40 Epoxy Vinyl Ester (EVE) was obtained from Ashland Inc. (Covington, Ky.) and used as received.

Example 1

Functionalization of Hydroxyapatite

Hexamethylene diisocyanate (HMDI) was used as the linker to tether dimethylaminobenzyl alcohol (DMOH) to the hydroxyl groups present on the surface of HA particles. The functionalization of HA particles followed established procedures (Liu, Q.; de Wijn, J. R.; van Blitterswijk, C. A., *Journal of Biomedical Materials Research* 1998, 40, 257). HA (5 g), dry DMF (75 mL), DBTL (0.075 mL) and HMDI (2.5 mL) were allowed to stir in a 500 mL round bottom flask for 8 h at 55° C. under $N_2$. DMOH (2 mL) or methanol was then added and the mixture was kept under the same conditions for an additional 5 h. The functionalized HA powder was separated by centrifugation and washed 3 times each with DMF and ethanol successively. The surface functionality of DMOH-modified hydroxyapatite (m-HA) was analyzed by infrared (IR) spectroscopy, and their IR spectra are compared in FIG. 3.

The grafting efficiency of m-HA was estimated from TGA results by comparing the mass loss when HMDI alone was grafted to HA and quenched with methanol. The TGA graphs are depicted in FIG. 4. Assuming the mass loss in the product was due to the $HMDI-CH_3OH$ grafting, the number of moles of HMDI grafted per gram HA can be calculated. Since HMDI was reacted with HA for the same period of time and under the same conditions in the synthesis of m-HA prior to addition of DMOH, the grafting efficiency of the DMOH to HA was calculated as a function of the number of moles of HMDI grafted to HA according to the following equation (Liu et al.):

$$G = W/N$$

where G is the grafting efficiency of DMOH, W is the mass of the grafted DMOH per gram of HA, and N is the number of moles of HMDI coupled to HA. Organic mass loss for the HMDI-CH$_3$OH functionalized HA was 4.6 wt %, corresponding to 3.9 wt % from the HMDI moiety and 0.7 wt % from the methoxy moiety. This mass loss was equivalent to 0.2 mmol HMDI per gram of HA. Total mass loss for m-HA was 10 wt %, from which 3.9 wt % likely is due to the HMDI moiety and the remaining 6.1 wt % likely is from the DMOH moiety. The calculated grafting density for DMOH was therefore 0.31 g/mmol.

Example 2

Analysis of Effect of Functionalized HA on Polymerization

The ability of m-HA particles to serve as an accelerant was evaluated in a simulated bone cement sample in which the accelerant was replaced by m-HA. Three samples, each containing 54.1 wt % PMMA beads, 5.4 wt % initiator VII, and 40.5 wt % HA were prepared. m-HA was used in one of the samples in the place of regular HA. MMA (2 mL) was then added to each sample, and DMA (0.02 mL) was added to one of the samples containing regular HA. The curing kinetics for each sample were then evaluated by dynamic differential scanning calorimetry (DSC) (25-200° C. at 10° C./min).

Compared to the sample containing no accelerant, significant polymerization acceleration was observed for the sample containing m-HA (FIG. 5). However, the rate of acceleration was slower than for the sample containing liquid DMA. Based on an estimation of 6.1 wt % DMOH in every sample of m-HA, the number of moles of accelerant in the sample activated by m-HA was calculated to be $3.06 \times 10^{-4}$ mol, while the number of moles of accelerant in the sample containing DMA was $1.58 \times 10^{-4}$ mol. One possible reason for the difference in activities observed between the two methods of acceleration may be the lack of mobility of the tethered accelerant molecules in the case of m-HA acceleration.

Example 3

Analysis of Thermal Stability of Initiators

Figure 6:
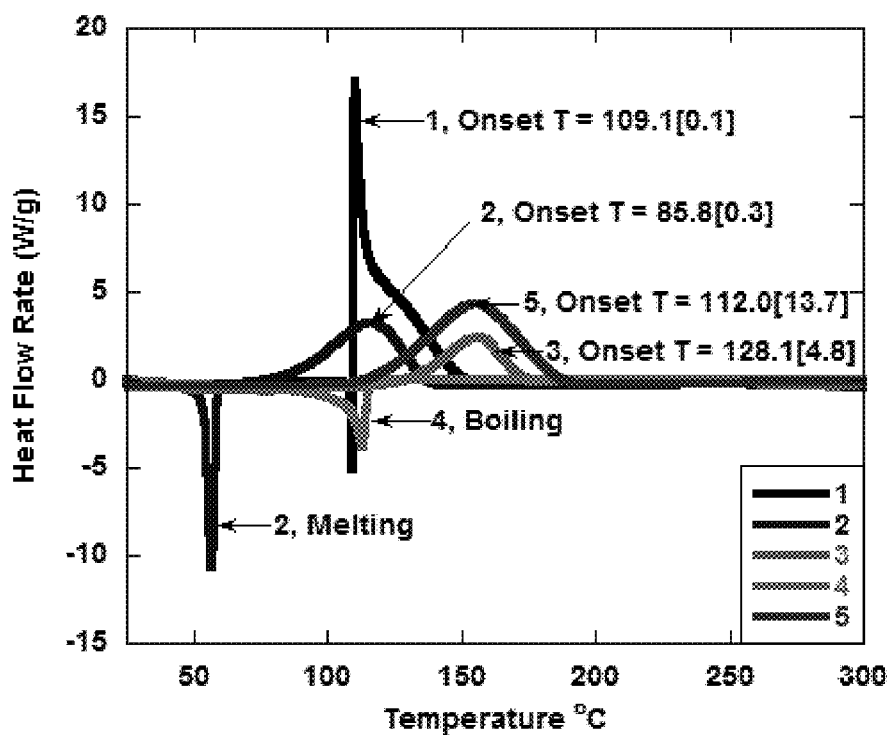
FIG. 6 depicts dynamic DSC data for various initiators.

The thermal behavior of each initiator was evaluated by dynamic Differential Scanning Calorimetry (DSC) experiments performed on a DSC821 instrument (Mettler-Toledo). The temperature range analyzed was 25° C.-300° C., with a heating rate of 10° C./min. Dynamic experiments were performed under nitrogen atmosphere, and all DSC experiments were performed in 40 µL aluminum crucibles. Average sample sizes were 5.66±2.66 mg for as-received samples and 2.26±0.85 mg for ground samples. Three trials were performed for each initiator. FIG. 6 depicts dynamic DSC data for initiators VII to XI, and Table 2 lists the average total heat and standard deviations for relevant thermal transitions as well as average onset temperatures.

TABLE 2

Thermal properties of free radical initiators

| Initiator | Heat of Decomposition (kJ/mol) | Total Heat 25° C.-300° C. (kJ/mol) | Average Onset T (° C.) |
|---|---|---|---|
| VII | N/A | 295.1[6.6] | 109.1[0.1] |
| VIII | 277.5[15.4] | 192.2[9.4] | 85.8[0.3] |
| IX | 107.7[8.3] | 107.7[8.3] | 128.1[4.8] |
| X | N/A | −49.4[3.3] | 109.2[1.0] |
| XI | 214.8[0.2] | 214.8[0.2] | 112.0[13.7] |

In general, the onset temperature of a thermal event is defined as the intersection between the tangent to the maximum rising slope of a DSC curve and the extrapolated sample baseline. A lower onset temperature of decomposition suggests more facile homolytic cleavage of peroxide initiators. The endotherms displayed by initiators VIII and X correspond to the heat of fusion (VIII) or heat of vaporization (X) (FIG. 6, Table 2). While initiator X exhibited a single thermal event, VIII exhibited distinct events corresponding to melting and decomposition respectively. Initiator X was observed to boil, but no decomposition was observed up to 300° C. In the case of VII, decomposition occurred adjacent to melting, and thus the heat of fusion could not be measured independently of the heat of decomposition. The data suggests that initiators IX and X are the most thermally stable of the initiators selected. While VII and VIII were the least thermally stable of selected initiators, their onset temperature for decomposition was high enough that they are not expected to decompose at processing and application temperatures for a self-healing bone cement.

Example 4

Analysis of Reactivity of Initiators

Figure 7:
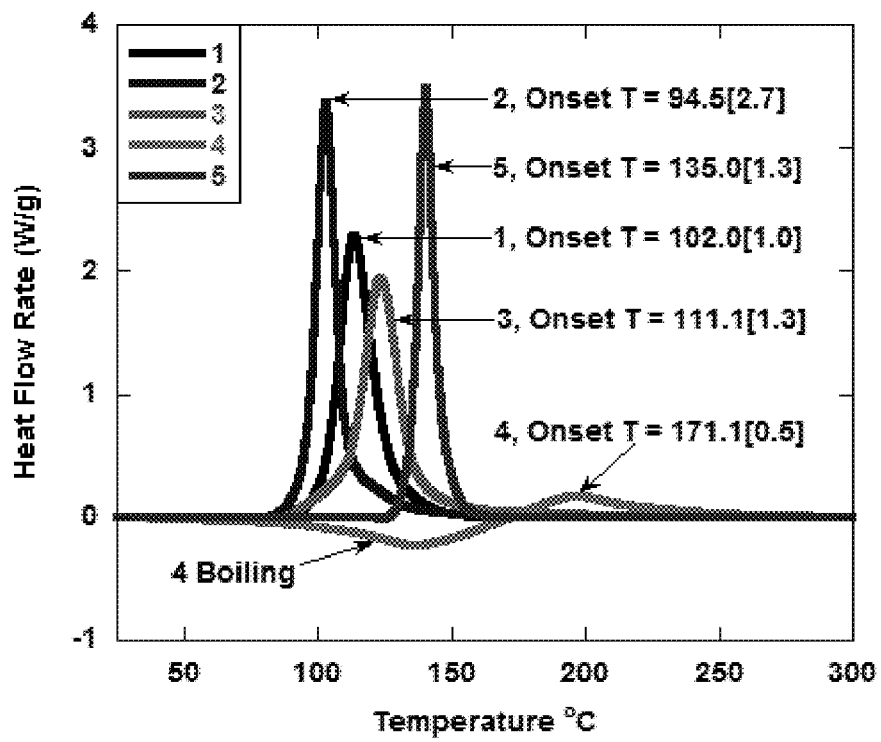
FIG. 7 depicts dynamic DSC data for the polymerization of Derakane 510A-40 epoxy vinyl ester resin with various initiators.

The reactivities of the initiators with Derakane® 510A-40 epoxy vinyl ester, a standard acrylic resin, were compared in the presence and absence of accelerants. The total heat of polymerization of the epoxy vinyl ester resin with each initiator was obtained by dynamic DSC evaluations of 11.80±3.56 mg samples of epoxy vinyl ester containing initiator ($4.13 \times 10^{-4}$ mol/g). Initiators were stirred into the resin for 5 minutes at 1,000 RPM using a mechanical stirrer prior to loading the sample into the DSC. To evaluate the reactivity of these initiators with various accelerants, the accelerants were added to separate resin samples already containing initiators at varying concentrations. Dynamic DSC evaluations were performed on 21.92±7.44 mg sample sizes using two concentration combinations of initiator and accelerant ($4.13 \times 10^{-4}$ mol/g of initiator with $8.25 \times 10^{-5}$ mol/g of accelerant, and $8.25 \times 10^{-5}$ mol/g of initiator with $4.13 \times 10^{-4}$ mol/g of accelerant). Samples with liquid accelerant were prepared by mixing initiator and resin for 5 minutes at 1,000 RPM, then adding accelerant by pipette, stirring for 15 seconds at 1,000 RPM, and loading the sample into the DSC within 118±20 seconds after addition of accelerant. For experiments with the solid accelerant (4,4'-methylene-bis(N,N-dimethyl aniline) that could not be added by pipette, initiator and accelerant were stirred into EVE separately and the two parts were mixed for 15 seconds just prior to loading the sample into the DSC. Samples were loaded within 103±9 seconds after combining and stirring the separate initiator and accelerant solutions together. Three trials were performed for each initiator. FIG. 7 depicts dynamic DSC data for the polymerization of Derakane 510A-40 epoxy vinyl ester resin with initiators VII to XI, and Table 3 lists the average total heat of polymerization and standard deviations, as well as average onset temperatures.

TABLE 3

Polymerization properties of free radical initiators

| Initiator | Heat of Polymerization 25° C.-300° C. (J/g) | Heat of Polymerization 25° C.-300° C. (kJ/mol) | Average Onset T (° C.) |
|---|---|---|---|
| VII | 240.4[9.7] | 56.2[2.3] | 102.0[1.0] |
| VIII | 251.0[7.6] | 100.1[3.0] | 94.5[2.7] |
| IX | 234.4[8.8] | 49.3[2.3] | 111.1[1.3] |
| X | 50.5[13.8] | 7.4[2.0] | 171.1[0.5] |
| XI | 168.1[14.5] | 32.6[2.8] | 135.0[1.3] |

As expected, in the absence of accelerants, the average onset temperatures for polymerization of the epoxy vinyl ester resin closely mirrored the average onset temperatures for decomposition, with initiator VIII exhibiting the lowest average onset temperature for polymerization at 94.5±2.7° C. and X exhibiting the highest at 171±0.5° C. (FIG. 7, Table 3).

Example 5

Isothermal Analysis of Initiators

To simulate the reactivity of various combinations of initiator and accelerant at body temperature, isothermal DSC experiments were performed at 38° C. Two additional temperatures (25° C. and 50° C.) were selected to facilitate more comprehensive evaluation of the temperature dependence of the initial rate of polymerization and the degree of monomer conversion. The isothermal experiments were performed at 25° C., 38° C., and 50° C., respectively, for 120 minutes on samples containing a mixture of Derakane® 510A-40 epoxy vinyl ester and either initiator VII or VIII. The initiator and accelerant concentrations used were the same as those used in the dynamic thermal analysis. Initiators were mixed with the resin for 5 minutes at 1,000 RPM, and 19.77±5.68 mg samples were loaded into the instrument within 119±21 seconds after mixing. Resin samples with varying concentrations of initiator (ranging from $8.25 \times 10^{-4}$ mol/g to $2.06 \times 10^{-4}$ mol/g) and accelerant (ranging from $4.13 \times 10^{-4}$ mol/g to $1.65 \times 10^{-3}$ mol/g) were evaluated by isothermal DSC at 38° C. (body temperature) for 120 minutes. Samples weighing 25.43±9.89 mg were prepared as above and loaded into the DSC within 98±21 seconds after addition of the accelerant.

Figure 8A:
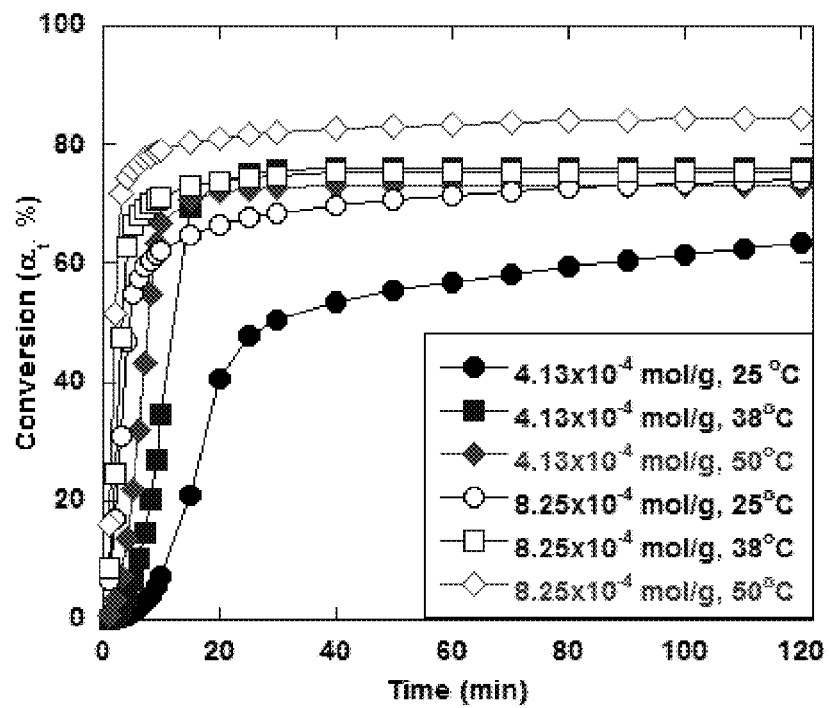
FIGS. 8A and 8B depict graphs of polymerization conversion for an epoxy vinyl ester resin using combinations of initiator VII and accelerant XII ($a$) and of initiator VIII and accelerant XII ($b$), at various accelerant concentrations and reaction temperatures.
Figure 8B:
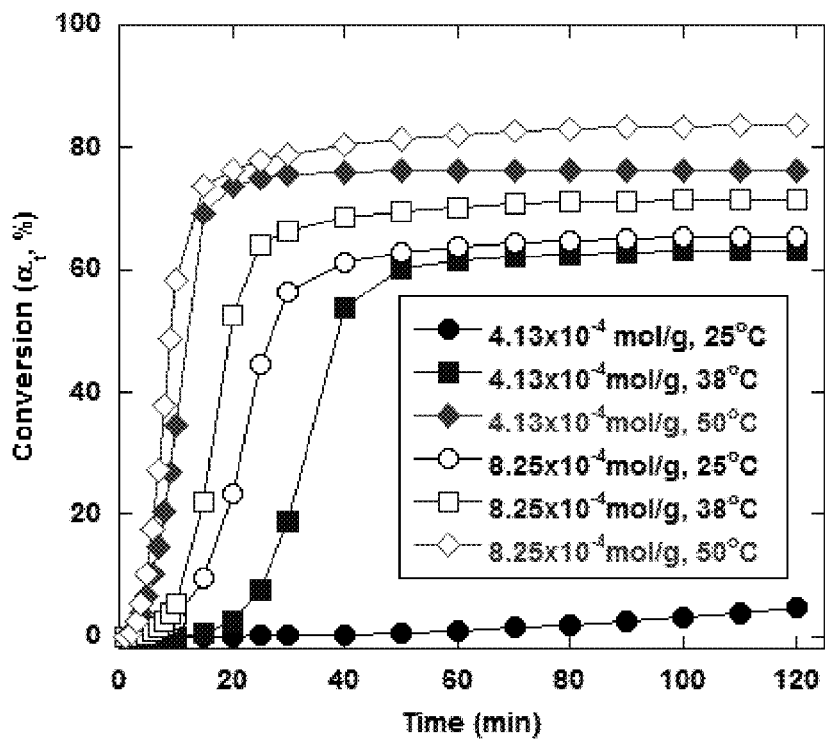

The initial rate of polymerization and degree of conversion with initiators VII and VIII were dependent on both temperature and concentration of initiator and accelerant (FIGS. 8A and 8B). For example, at 25° C., initiator VII exhibited hardly any conversion of monomer at the lower concentrations of initiator and accelerant (FIG. 8B), while initiator VII exhibited almost 60% conversion after 2 hours under the same conditions. Determination of temperature and concentration dependence is essential in determining which initiator/accelerant combination is most likely to initiate polymerization of a specified monomer in situ before the monomer is lost by diffusion into the biological system. Since initiators IX, X and XI exhibited minimal reactivities, these isothermal experiments and the following stoichiometric dependence experiments were only performed with initiators VII and VIII.

Example 6

Reactivity of Initiators With Accelerants

Dynamic DSC experiments were used to determine the reactivity of initiators VII to XI with accelerants XII to XIV in the polymerization of Derakane 510A-40 epoxy vinyl ester resin. The temperature range analyzed was 25° C.-300° C., with a heating rate of 10° C./min. The accelerants were chosen to simulate the steric and electronic properties of accelerants tethered to the surface of HA particles. Two sets of initiator/accelerant combinations were analyzed—1) $4.13 \times 10^{-4}$ mol/g resin of initiator and $8.25 \times 10^{-5}$ mol/g resin of accelerant, and 2) $8.25 \times 10^{-5}$ mol/g resin of initiator and $4.13 \times 10^{-4}$ mol/g resin of accelerant. Three trials were performed for each combination of initiator and accelerant. Table 4 lists the average onset temperatures for each combination.

TABLE 4

Onset temperatures of polymerization using different types and concentrations of initiators and accelerants

| | Average Onset Temperature (° C.) | | |
|---|---|---|---|
| Initiator ($4.13 \times 10^{-4}$ mol/g) | Accelerant XII ($8.25 \times 10^{-5}$ mol/g) | Accelerant XIII ($8.25 \times 10^{-5}$ mol/g) | Accelerant XIV ($8.25 \times 10^{-5}$ mol/g) |
| VII | 61 | 37 | 36 |
| VIII | 92 | 71 | 65 |
| IX | 116 | 112 | 110 |
| X | 175 | 172 | 159 |
| XI | 136 | 135 | 127 |
| Initiator ($8.25 \times 10^{-5}$ mol/g) | Accelerant XII ($4.13 \times 10^{-4}$ mol/g) | Accelerant XIII ($4.13 \times 10^{-4}$ mol/g) | Accelerant XIV ($4.13 \times 10^{-4}$ mol/g) |
| VII | 42 | <25 | <25 |
| VIII | 70 | 49 | 42 |
| IX | 116 | 101 | 61 |
| X | 170 | 163 | 151 |
| XI | 131 | 124 | 115 |

In general, the addition of accelerants either lowered, or had no effect on the onset temperature of polymerization. The onset temperature of polymerization with initiator VII was most affected by the addition of accelerant. As the concentration of initiator and accelerant increased, the onset temperature of polymerization decreased (Table 4). Initiator VIII did not demonstrate a high level of reactivity with accelerant XII at the lower concentration, as indicated by a minimal change in onset temperature relative to thermal polymerization of the epoxy vinyl ester resin (compare Table 3 to Table 4). However, when the concentration of initiator VIII was increased two-fold and that of accelerant XII was increased five-fold, the onset temperature significantly decreased to 70.1° C. In addition, initiators VII and VIII appeared to react better with accelerants XIII and XIV than with accelerant XII. This observation is consistent with increased nucleophilicity of the tertiary amine due to donation of electron density from the methyl functionality in the para position of the benzene ring of accelerant XIII by hyperconjugation. Similarly, accelerant XIV may demonstrate a higher level of reactivity with these initiators as a result of its bifunctionality.

The average onset temperature for polymerization with initiator IX decreased with the addition of accelerant, but did not decrease with increased concentration of initiator IX and accelerant. Initiator X boiled off in each evaluation except for when it was paired with accelerant XIV, and onset temperature of polymerization did not change significantly with increasing concentration of initiator X and accelerant. Similarly, initiator XI exhibited consistently high onset temperatures of polymerization that were not affected by the addition and concentration of accelerant. These observations suggest that initiator X and XI may not be reactive enough for the system envisioned.

Example 7

Effect of Accelerant/Initiator Ratios on Initial Polymerization Rates

When a crack propagates through a self-healing bone cement based on free radical polymerization, healing agents released into the crack plane may mix at less than desirable concentrations. Thus, in comparing initiators for application in a self-healing system, the effect of stoichiometry on the eventual polymerization was investigated. The polymerization of the epoxy vinyl ester resin at 38° C. was evaluated using a range of accelerant/initiator concentration ratios ([A]/[I]).

Figure 9A:
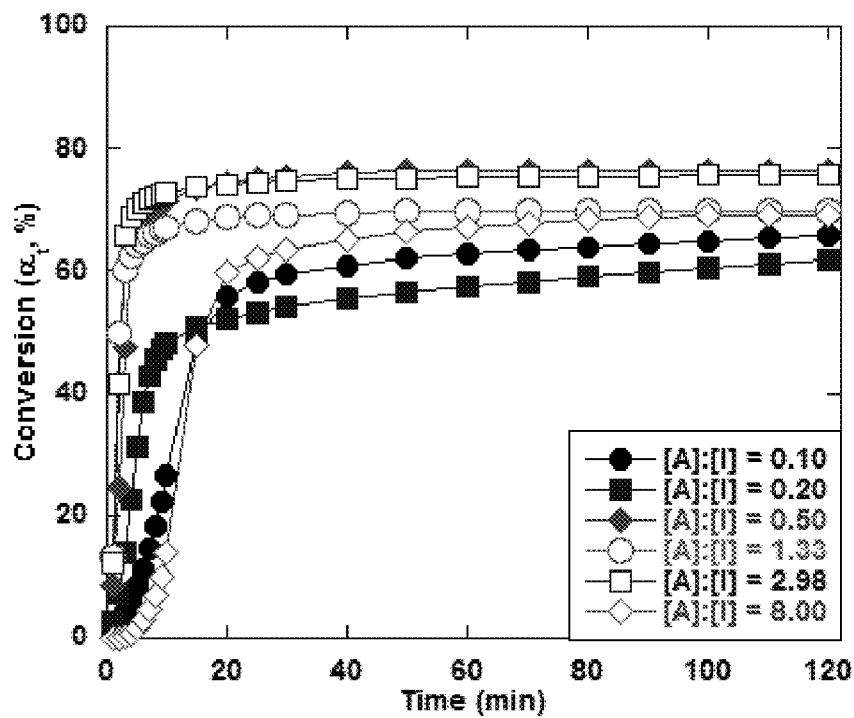
FIGS. 9A and 9B depicts graphs of polymerization conversion for an epoxy vinyl ester resin using various accelerant:initiator ratios ([A]:[I]) of accelerant XII and initiator VII ($a$) and of accelerant XII and initiator VIII ($b$).
Figure 9B:
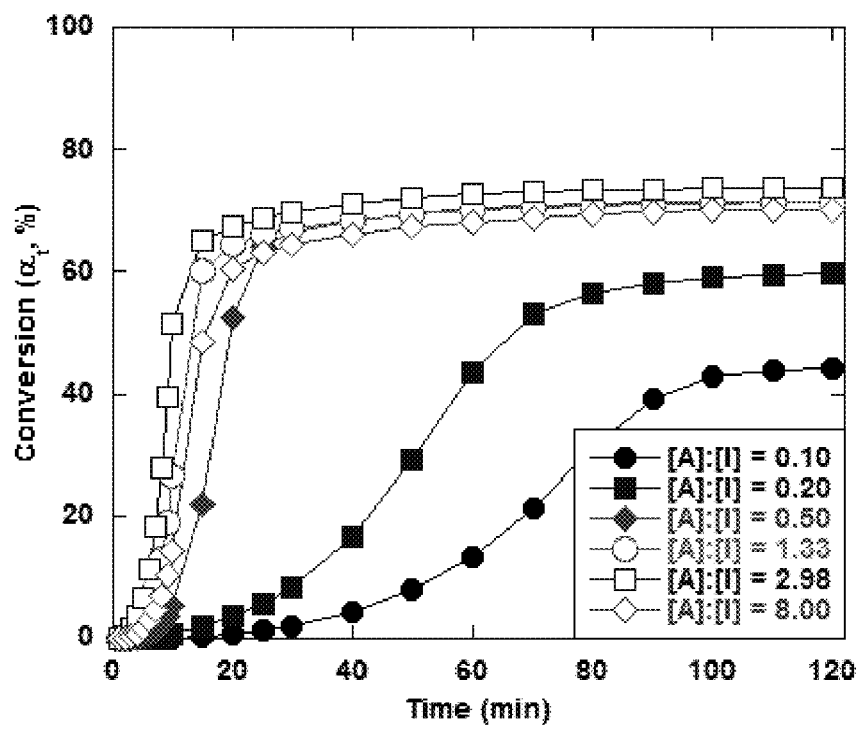

The ratio of [A]/[I] had a minimal effect on polymerizations initiated by VII at lower concentrations of accelerant (lower ratios) (FIGS. 9A and 9B). However, at higher [A]/[I] for initiator VII, polymerization rate and degree of conversion decreased. Thus, as long as the concentration of accelerant XII is not too high, it appears that polymerization in the crack plane will occur rapidly. This observation is consistent with the work of Vazquez and coworkers who demonstrated that when accelerants are present at high concentrations, they can act as polymerization inhibitors (Vazquez, B.; Elvira, C.; Levenfeld, B.; Pasqual, B.; Goñi, I.; Gurruchaga, M.; Ginebra, M. P.; Gil, F. X.; Planell, J. L.; Liso, P. A.; Rebuelta, M.; San Roman, J., *Journal of Biomedical Materials Research* 1997, 34, 129).

Optimal [A]/[I] ratios ranged from 0.50-2.98. Initial polymerization rates for optimal stoichiometric concentrations of initiator VIII were slower than for initiator VI (FIG. 9B). However, while the initial rate of polymerization and degree of conversion of initiator VII was observed to decrease significantly at [A]/[I]=8.00, initiator VIII did not display as sharp a change in initial rate of polymerization and degree of conversion at this concentration ratio. The rationale that polymerization must occur at a fast rate to avoid loss of monomer to the biological system favors initiator VII over initiator VIII as a candidate for the system envisioned. On the other hand, when a crack ruptures embedded microcapsules in a self-healing system, releasing its contents into the crack plane, parameters such as viscosity, mixing issues, and varying rates of flow can cause the mixture in the crack plane to be at less than ideal stoichiometric concentrations. Thus, the fact that initiator VIII is less dependent upon the ratios of accelerant to initiator concentration could compensate for the slower initial polymerization rates and lower degree of conversion observed in polymerizations initiated with this initiator.

Example 8

Effect of Accelerant/Initiator Ratios on Mechanical Properties

Figure 10:
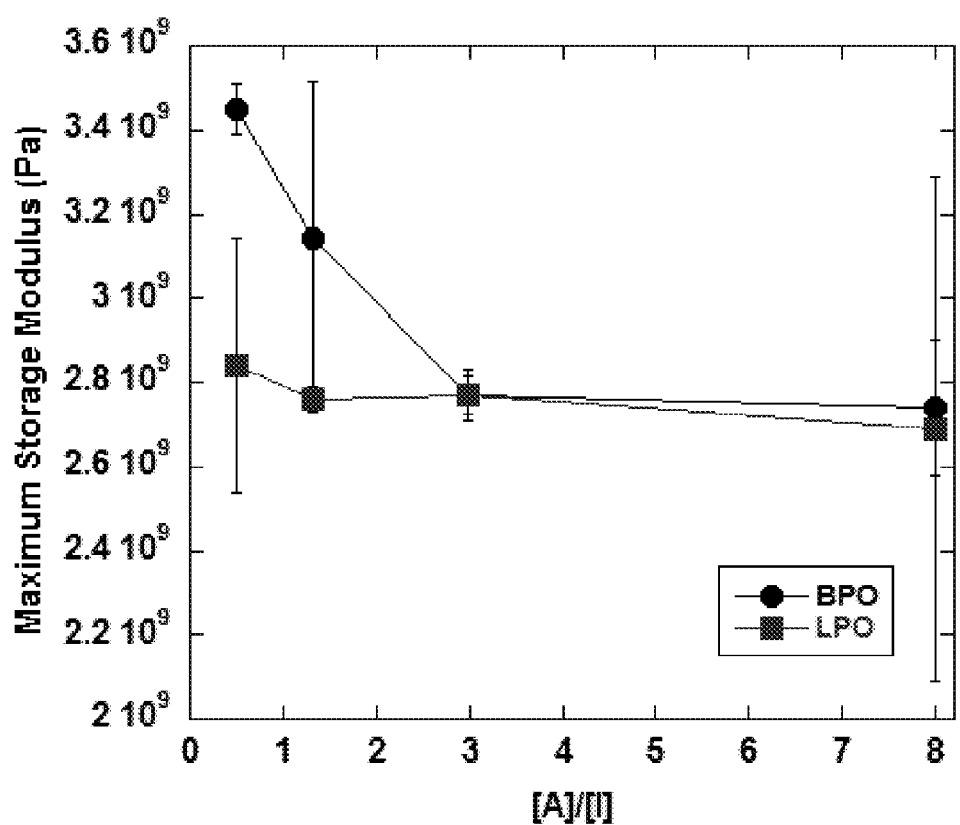
FIG. 10 depicts graphs of the average modulus for an epoxy vinyl ester formed versus the various accelerant:initiator ratios ([A]:[I]) used, where the accelerant was XII and the initiator was either VII (BPO) or VIII (LPO).

The average moduli of resin samples cured with varying concentrations of initiators VII and VIII and accelerant XII were measured in three point bend dynamic mechanical analysis (DMA) experiments. The type of initiator used, as well as the [A]/[I] ratio, did not appear to have a significant effect on the modulus of the resulting polymerized resin. On average, resins prepared with initiator VIII exhibited slightly lower average moduli than those prepared with initiator VII (FIG. 10). While the modulus of samples prepared with initiator VIII reached a maximum at an [A]/[I] ratio of 1.33, a gradual increase was observed for samples prepared with initiator VII, with the maximum average modulus occurring at an [A]/[I] ratio of 8.00. Overall, these results suggest that the average modulus is less dependent on the [A]/[I] ratio when initiator VII is used as the initiator.

Example 9

Qualitative Monomer Reactivity Screening

Initiator VII (1 wt %, 2 wt %) and DMA (0.1 wt %, 0.5 wt %) were added to 5 mL samples of monomer mixtures in 20 mL scintillation vials. The contents of the vials were stirred using a vortex. The samples were monitored every 5 min for the first 30 min, followed by every hour up to 4 h, then at 8 h, 12 h and 24 h. The physical characteristics of the samples were observed and descriptions recorded at the times specified.

The screening experiments referred to here were qualitative and were simply aimed at determining reactivity of the monomer or blend of monomers to a combination of BPO (1 wt % or 2 wt %) and DMA (0.1 wt % or 0.5 wt %).

The results of these screening experiments have been summarized in Tables 5-7. In general, most mixtures polymerized at the higher concentration of initiator (2 wt %) and accelerant (0.5 wt %). Ethylene glycol dimethacrylate (EGDMA) appeared to be the most versatile monomer at these concentrations of initiator and accelerant, yielding a hard cross-linked polymer in 4 h or less in all combinations with MMA, BMA and styrene.

TABLE 5

| Copolymerization of Monomer III (Bis-GMA) | | | |
|---|---|---|---|
| Monomer Added | Amount added (wt %) | Time to Polymerization | Description of Polymer |
| Bis-GMA Experiments: 1 wt % BPO and 0.1 wt % DMA added | | | |
| MMA | 20 | 24 h | incomplete polymerization |
| MMA | 30 | 24 h | incomplete polymerization |
| MMA | 40 | 2 h | hard polymer |
| MMA | 50 | 4 h | hard polymer |
| MMA | 60 | N/A | N/A |
| MMA | 70 | N/A | N/A |
| MMA | 80 | N/A | N/A |
| BMA | 20 | 24 h | incomplete polymerization |

TABLE 5-continued

Copolymerization of Monomer III (Bis-GMA)

| Monomer Added | Amount added (wt %) | Time to Polymerization | Description of Polymer |
|---|---|---|---|
| BMA | 30 | 24 h | incomplete polymerization |
| BMA | 40 | 24 h | incomplete polymerization |
| BMA | 50 | 24 h | incomplete polymerization |
| BMA | 60 | 24 h | incomplete polymerization |
| BMA | 70 | | |
| BMA | 80 | | |
| Styrene | 20 | 24 h | incomplete polymerization |
| Styrene | 30 | 24 h | incomplete polymerization |
| Styrene | 40 | 24 h | incomplete polymerization |
| Styrene | 50 | 24 h | incomplete polymerization |
| Styrene | 60 | 24 h | incomplete polymerization |
| Styrene | 70 | 24 h | hard polymer |
| Styrene | 80 | 24 h | hard polymer |
| Bis-GMA Experiments: 2 wt % BPO and 0.5 wt % DMA added | | | |
| MMA | 20 | 24 h | incomplete polymerization |
| MMA | 30 | 30 min | incomplete polymerization |
| MMA | 40 | 30 min | hard polymer |
| MMA | 50 | 30 min | hard polymer |
| MMA | 60 | 30 min | hard polymer |
| MMA | 70 | 30 min | hard polymer |
| MMA | 80 | 30 min | hard polymer |
| BMA | 20 | 24 h | incomplete polymerization |
| BMA | 30 | 30 min | incomplete polymerization |
| BMA | 40 | 30 min | incomplete polymerization |
| BMA | 50 | 30 min | incomplete polymerization |
| BMA | 60 | 30 min | incomplete polymerization |
| BMA | 70 | 2 h | hard polymer |
| BMA | 80 | 2 h | hard polymer |
| Styrene | 20 | 24 h | incomplete polymerization |
| Styrene | 30 | 30 min | incomplete polymerization |
| Styrene | 40 | 30 min | incomplete polymerization |
| Styrene | 50 | 30 min | incomplete polymerization |
| Styrene | 60 | 2 h | incomplete polymerization |
| Styrene | 70 | 2 h | hard polymer |
| Styrene | 80 | 2 h | hard polymer |

TABLE 6

Copolymerization of Monomer IV (TMPTMA)

| Monomer Added | Amount added (wt %) | Time to Polymerization | Description of Polymer |
|---|---|---|---|
| TMPTMA Experiments: 1 wt % BPO and 0.1 wt % DMA added | | | |
| MMA | 20 | N/A | N/A |
| MMA | 30 | N/A | N/A |
| MMA | 40 | N/A | N/A |
| MMA | 50 | N/A | N/A |
| MMA | 60 | N/A | N/A |
| MMA | 70 | N/A | N/A |
| MMA | 80 | N/A | N/A |
| BMA | 20 | N/A | N/A |
| BMA | 30 | N/A | N/A |
| BMA | 40 | N/A | N/A |
| BMA | 50 | N/A | N/A |
| BMA | 60 | N/A | N/A |
| BMA | 70 | N/A | N/A |
| BMA | 80 | N/A | N/A |
| Styrene | 20 | N/A | N/A |
| Styrene | 30 | N/A | N/A |
| Styrene | 40 | N/A | N/A |
| Styrene | 50 | N/A | N/A |
| Styrene | 60 | 24 h | incomplete polymerization |
| Styrene | 70 | 24 h | incomplete polymerization |
| Styrene | 80 | 24 h | incomplete polymerization |
| TMPTMA Experiments: 2 wt % BPO and 0.5 wt % DMA added | | | |
| MMA | 20 | 30 min | hard polymer |
| MMA | 30 | 30 min | hard polymer |
| MMA | 40 | 30 min | hard polymer |
| MMA | 50 | 30 min | hard polymer |
| MMA | 60 | 30 min | hard polymer |
| MMA | 70 | 30 min | hard polymer |
| MMA | 80 | 30 min | hard polymer |
| BMA | 20 | 30 min | N/A |
| BMA | 30 | 30 min | N/A |
| BMA | 40 | 30 min | N/A |
| BMA | 50 | 24 h | incomplete polymerization |
| BMA | 60 | 24 h | incomplete polymerization |
| BMA | 70 | 24 h | incomplete polymerization |
| BMA | 80 | 24 h | incomplete polymerization |
| Styrene | 20 | 30 min | hard polymer |
| Styrene | 30 | 30 min | hard polymer |
| Styrene | 40 | 30 min | hard polymer |
| Styrene | 50 | 4 h | N/A |
| Styrene | 60 | 4 h | incomplete polymerization |
| Styrene | 70 | 4 h | hard polymer |
| Styrene | 80 | 4 h | hard polymer |

TABLE 7

Copolymerization of Monomer V (EGDMA)

| Monomer Added | Amount added (wt %) | Time to Polymerization | Description of Polymer |
|---|---|---|---|
| EGDMA Experiments: 1 wt % BPO and 0.1 wt % DMA added | | | |
| MMA | 20 | N/A | N/A |
| MMA | 30 | N/A | N/A |
| MMA | 40 | N/A | N/A |
| MMA | 50 | N/A | N/A |
| MMA | 60 | N/A | N/A |
| MMA | 70 | N/A | N/A |
| MMA | 80 | N/A | N/A |
| BMA | 20 | N/A | N/A |
| BMA | 30 | N/A | N/A |
| BMA | 40 | N/A | N/A |
| BMA | 50 | N/A | N/A |
| BMA | 60 | N/A | N/A |
| BMA | 70 | N/A | N/A |
| BMA | 80 | N/A | N/A |
| Styrene | 20 | N/A | N/A |
| Styrene | 30 | 24 h | incomplete polymerization |
| Styrene | 40 | 24 h | incomplete polymerization |
| Styrene | 50 | 24 h | incomplete polymerization |
| Styrene | 60 | 24 h | incomplete polymerization |
| Styrene | 70 | 24 h | incomplete polymerization |
| Styrene | 80 | 24 h | incomplete polymerization |
| EGDMA Experiments: 2 wt % BPO and 0.5 wt % DMA added | | | |
| MMA | 20 | 30 min | hard polymer |
| MMA | 30 | 30 min | hard polymer |
| MMA | 40 | 30 min | hard polymer |
| MMA | 50 | 30 min | hard polymer |
| MMA | 60 | 30 min | hard polymer |
| MMA | 70 | 30 min | hard polymer |
| MMA | 80 | 30 min | hard polymer |
| BMA | 20 | 30 min | hard polymer |
| BMA | 30 | 30 min | hard polymer |
| BMA | 40 | 30 min | hard polymer |
| BMA | 50 | 30 min | hard polymer |
| BMA | 60 | 2 h | hard polymer |
| BMA | 70 | 2 h | hard polymer |
| BMA | 80 | 2 h | hard polymer |
| Styrene | 20 | 2 h | hard polymer |
| Styrene | 30 | 2 h | hard polymer |
| Styrene | 40 | 2 h | hard polymer |
| Styrene | 50 | 2 h | hard polymer |
| Styrene | 60 | 4 h | hard polymer |

TABLE 7-continued

Copolymerization of Monomer V (EGDMA)

| Monomer Added | Amount added (wt %) | Time to Polymerization | Description of Polymer |
|---|---|---|---|
| Styrene | 70 | 4 h | hard polymer |
| Styrene | 80 | 4 h | hard polymer |

Example 10

Simulated Bone Cement Sample Preparation and Testing

Simulated samples of bone cement were prepared from two parts and were based on the composition of Surgical Simplex® P. The solid part included a total of 40 g of powder, of which 1.7 wt % was initiator VII, and the remainder was PMMA (MW=300,000 g/mol, Polysciences). The liquid part (20 mL) included DMA (2.6 vol %), and the remainder was MMA. The two parts were mixed together, and the mixture was quickly transferred to a TDCB mold, which was made of either Delrin® or Teflon®. The samples were allowed to cure at room temperature for 24 hours, after which they were pin-loaded to failure at 5 μms$^{-1}$ under displacement control. After failure, a healing agent mixture (0.03 mL) was injected into the crack plane. The samples were allowed to heal at room temperature for 24 hours before testing to failure again. Preliminary reference test results are summarized in Table 8.

Reference tests performed by injecting MMA alone into the crack plane of virgin simulated bone cement TDCB samples exhibited an average healing efficiency of about 47%. Similar observations of crack healing have been attributed to chain entanglement in the crack plane promoted by the solvent-induced depression of the glass transition temperature ($T_g$) in the crack plane (Wang, P.; Lee, S.; Harmon, J. P., *Journal of Polymer Science, Part B: Polymer Physics* 1994, 32, 1217). This phenomenon is commonly referred to as solvent welding. The addition of initiator VII (2 wt %) and DMA (0.5 wt %) to the MMA injected into the crack plane of virgin simulated bone cement samples resulted in polymerization of the MMA in the crack plane and a corresponding increase in the healing efficiency to 74%. No solvent welding was observed for samples in which Bis-GMA/MMA or Bis-GMA/BMA mixtures were injected into the crack plane. However when BPO and DMA were added to these polymerizer mixtures at the same concentrations as above, healing efficiencies of 59% and 40% respectively were observed. Though they exhibited lower healing performance in reference tests, mixtures such as Bis-GMA/MMA are more likely to be used as polymerizers than neat monomers such as MMA, as they are expected to exhibit less volume shrinkage.

Example 11

Polymerizations with Reactants in Capsules

Capsules were prepared containing either monomer IV (alone or in combination with bisphenol-A acrylate), initiator VII, initiator VIII, or accelerant XII. Table 9 lists the compositions of these capsules.

TABLE 8

Healing performance of bone cement mimic compositions

| Multifunctional Monomer | Multifunctional Monomer | Initiator BPO (wt %) | Accelerant DMA (wt %) | Average Peak Virgin Fracture | Average Peak Healed Fracture | Average Healing Efficiency ($\eta_{avg}$, %) |
|---|---|---|---|---|---|---|
| N/A | MMA | 0 | 0 | 138.8 [19.3] | 70.6 [1.1] | 47 |
| N/A | MMA | 2 | 0.5 | 160.2 [21.2] | 119.0 [13.1] | 74 |
| Bis-GMA | MMA | 0 | 0 | 140.6 [9.5] | 0 | 0 |
| Bis-GMA | MMA | 2 | 0.5 | 163.5 [34.0] | 96.8 | 59 |
| Bis-GMA | BMA | 0 | 0 | 140.6 [16.7] | 0 | 0 |
| Bis-GMA | BMA | 2 | 0.5 | 175.3 [14.0] | 69.4 [6.5] | 40 |

TABLE 9

| Active Agent | Initiator VII | Initiator VIII | Monomer IV | Bisphenol-A acrylate | Accelerant XII | Solvent |
|---|---|---|---|---|---|---|
| Initiator | 9.9 wt % in PA | | | | | 60 g PA |
| Initiator | 8.8 wt % in EPA | | | | | 60 g EPA |
| Initiator | | 4.3 wt % in hexyl acetate | | | | 60 g hexyl acetate |
| Monomer | | | Pure IV | | | 0 |
| Monomer | | | 36.0 g | 12.0 g | | 12.1 g EPA |
| Accelerant | | | | | 10 wt % in solvent | Dibutyl phthalate |

Monomer IV was mixed with the initiator capsules containing 9.9 wt % initiator VII in PA and with the accelerant capsules containing 10 wt % accelerant XII at various ratios, and each mixture was polymerized. Qualitative results are listed in Table 10.

TABLE 10

Polymerization of monomer IV with initiator and accelerant capsules

| Monomer (g) | Initiator Capsules (g) | Accelerant Capsules (g) | Result |
|---|---|---|---|
| 0.976 | 0.108 | 0.012 | poor |
| 1.010 | 0.207 | 0.032 | Good |
| 0.993 | 1.04 | 0.54 | BEST |
| 1.020 | 0.985 | 0.97 | good |

The monomer capsules containing pure monomer IV were mixed with the initiator capsules containing 8.8 wt % initiator VII in EPA and with one small drop of DMPT accelerant, and each mixture was polymerized. Qualitative results are listed in Table 11.

TABLE 11

Polymerization of monomer capsules with initiator capsules

| Monomer Capsules (g) | Initiator Capsules (g) | Result |
|---|---|---|
| 0.26 | 0.14 | Mostly uncured, pockets of very dense polymer |
| 0.55 | 0.13 | Some uncured at edges of film |
| 1.05 | 0.11 | Best adhesion, good film |

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A composite material precursor composition, comprising:
   a matrix precursor;
   a first plurality of capsules comprising a liquid polymerizer;
   an activator,
      where the liquid polymerizer polymerizes when in contact with the activator; and
   a plurality of functionalized particles comprising particles having a surface, and a functional group immobilized on the surface of the particles;
   where the functional group comprises an accelerant for the polymerization of the liquid polymerizer.

2. The composition of claim 1, where
   the liquid polymerizer comprises at least one of an acrylate monomer and an alkylacrylate monomer, and
   the activator comprises a free-radical initiator.

3. The composition of claim 2, where the
   functional group comprises a N,N-dimethylaniline group.

4. The composition of claim 3, where the particles comprise hydroxyapatite.

5. The composition of claim 4, where
   the liquid polymerizer comprises MMA,
   the initiator comprises BPO, and
   the functionalized particles comprise dimethylaminobenzyl alcohol-modified hydroxyapatite.

6. The composition of claim 2, where the matrix precursor comprises a precursor for PMMA.

7. The composition of claim 2, where the liquid polymerizer comprises
   at least one monomer selected from the group consisting of MMA and BMA, and
   at least one monomer selected from the group consisting of Bis-GMA, TMPTMA and EGDMA.

8. The composition of claim 2, where the initiator comprises a peroxide initiator.

9. The composition of claim 2, further comprising activator particles comprising the initiator.

10. A composite material, comprising:
    a solid polymer matrix;
    a first plurality of capsules in the solid polymer matrix,
       the first plurality of capsules comprising a liquid polymerizer;
    an activator in the solid polymer matrix,
       where the liquid polymerizer polymerizes when in contact with the activator; and
    a plurality of functionalized particles in the solid polymer matrix,
       the functionalized particles comprising particles having a surface, and a functional group immobilized on the surface of the particles,
       where the functional group comprises an accelerant for the polymerization of the liquid polymerizer in the solid polymer matrix.

11. The composite material of claim 10, where
    the liquid polymerizer comprises at least one of an acrylate monomer and an alkylacrylate monomer, and
    the activator comprises a free-radical initiator.

12. A method of making a composite material, comprising:
    combining ingredients comprising
       a matrix precursor,
       a first plurality of capsules comprising a liquid polymerizer, an activator, where the liquid polymerizer polymerizes when in contact with the activator, and a plurality of functionalized particles comprising particles having a surface, and a functional group immobilized on the surface of the particles, where the functional group comprises an accelerant for the polymerization of the liquid polymerizer; and solidifying the matrix precursor to form a solid polymer matrix.

13. The method of claim 12, where the functional group comprises a N,N-dimethylaniline group.

14. The method of claim 12, where the particles comprise hydroxyapatite.

15. The method of claim 12, where the liquid polymerizer comprises at least one monomer selected from the group consisting of MMA and BMA, and at least one monomer selected from the group consisting of Bis-GMA, TMPTMA and EGDMA.

16. The method of claim 12, where the activator comprises a peroxide initiator.

17. The composite material of claim 10, where the functional group comprises a N,N-dimethylaniline group.

18. The composite material of claim 10, where the particles comprise hydroxyapatite.

19. The composite material of claim 10, where the liquid polymerizer comprises at least one monomer selected from the group consisting of MMA and BMA, and at least one monomer selected from the group consisting of Bis-GMA, TMPTMA and EGDMA.

20. The composite material of claim 10, where the activator comprises a peroxide initiator.

* * * * *